United States Patent [19]

Young

[11] Patent Number: 4,693,992
[45] Date of Patent: Sep. 15, 1987

[54] BACITRACIN-METAL-POLYETHER ANTIBIOTIC COMPLEXES

[75] Inventor: Vernon V. Young, Terre Haute, Ind.

[73] Assignee: International Minerals & Chemical Corp., Terre Haute, Ind.

[21] Appl. No.: 769,066

[22] Filed: Aug. 26, 1985

[51] Int. Cl.[4] .................. A61K 37/02; A61K 31/70
[52] U.S. Cl. .................................. 514/11; 514/25; 514/30
[58] Field of Search ........................ 514/25, 30, 11

[56] References Cited

U.S. PATENT DOCUMENTS

| 4,086,345 | 4/1978 | Garzia et al. | 424/251 |
| 4,302,450 | 11/1981 | Comai et al. | 424/251 |
| 4,447,421 | 5/1984 | Klothen | 514/30 |
| 4,478,935 | 10/1984 | Williams et al. | 514/25 |

FOREIGN PATENT DOCUMENTS 102636  8/1979  Poland.

OTHER PUBLICATIONS

Chem. Abstr., vol. 89, (1978), 40962.

Kirk-Othmer Encyclopedia of Chemical Technology, 2nd Ed., vol. 16, pp. 315–319 and 337–345 (1968).
Polyether Antibiotics, vol. 1, edited by John W. Westley, Marcel Decker, Inc., New York and Bsel, pp. v–xi (1982).
Craig et al., Biochem., 8:2348–2356 (1969).
Merck Index, 10th Ed., Ref. 937 (1983).
Westley, Advances in Applied Microbiology, 22:177–223 (1977).
J. W. Westley et al., J. Am. Chem. Soc., 99:18 (1977).
Froyshov, Chimica Acta, 98:137–139 (1978).
Westley, Polyether Antibiotics, vol. 1 (1982).

Primary Examiner—Delbert R. Phillips
Attorney, Agent, or Firm—George R. Repper; Thomas L. Farquer

[57] ABSTRACT

Antibiotic-metal complexes contain bacitracin, a nontoxic, complex-forming metal and a polyether antibiotic are disclosed. The complexes are useful (1) for promoting growth in poultry and mammals, (2) for controlling swine dysentery, (3) modifying rumen fluid by decreasing the acetate to propionate (A/P) ratio, (4) controlling coccidiosis in birds, and (5) purifying bacitracin or a bacitracin-metal salt.

17 Claims, No Drawings

BACITRACIN-METAL-POLYETHER ANTIBIOTIC COMPLEXES

BACKGROUND OF THE INVENTION

The present invention relates to bacitracin-metal-polyether antibiotic complexes and their uses in (1) purifying bacitracin, (2) promoting growth in birds and mammals, (3) modifying rumen fluid by decreasing the acetate/propionate (A/P) ratio in ruminant animals, (4) controlling swine dysentery and (5) controlling coccidiosis in birds and mammals. Additionally, the present invention relates to a method of preparing bacitracin-metal-polyether antibiotic complexes.

Bacitracins are a well-known group of peptide antibiotics produced by strains of *Bacillus licheniformis* and *Bacillus subtilis*. Plain or regular bacitracin is a mixture of bacitracin peptides including bacitracin A, bacitracin B and bacitracin F. Bacitracin A is the major microbiologically active component of bacitracin. Bacitracin B is also microbiologically active while bacitracin F, the oxidation product of bacitracins A and B, is microbiologically inactive. Bacitracin is useful in standard antibiotic applications including use as growth-promoting animal feed additive.

Polyether antibiotics are also a well-known group of antibiotics which have long been used in veterinary applications i.e., as growth-promoting agents and coccidiostats. These antibiotics are known to form complexes with numerous monovalent and divalent metal ions (*Polyether Antibiotics—Naturally Occurring Acid Ionophores*, Vol. 2, J. W. Westley, Ed., Marcel Dekker, Inc., 1983, pp. 1-15), and sodium lasolocid, a commercially available polyether antibiotic, is known to form crystalline complexes with certain catecholamines (Westley, J. W., *J. Am. Chem. Soc.*, 99, 6057 (1977)).

SUMMARY OF INVENTION

In accordance with the present invention, bacitracin-metal-polyether antibiotic complexes are formed by combining, under complex-forming conditions, bacitracin, a polyether antibiotic and a non-toxic complex-forming metal ion. The complex may be recovered from the reaction mixture in solid form by precipitation from the reaction mixture.

The present complexes have been found to have a variety of uses, such as (1) controlling swine dysentery, (2) modifying rumen fluid by decreasing the A/P ratio, thereby improving rumen fermentation efficiency in ruminant animals, (3) promoting growth in birds and mammals, and (4) controlling coccidiosis in birds, and (5) purifying microbiologically active bacitracin.

DETAILED DESCRIPTION OF THE INVENTION

When used herein, the term "promoting growth" or any variations thereof, is meant to encompass an increase in body weight gain (increased growth rate) exhibited by a bird or mammal in response to administration of the present complexes at effective dosages, as compared to a control.

The term "feed utilization efficiency", when used herein, is meant to encompass a decrease in the ratio of units of feed required to produce a unit of gain or to maintain body weight of a bird or mammal in response to administration of the present complexes at effective dosages, as compared to a control.

The term "controlling swine dystentery", when used herein, is meant to encompass both prophylactic and therapeutic uses of the present complexes in swine for the prevention and treatment of active infections of swine dysentery.

The term "controlling coccidiosis" when used herein, is meant to encompass both prophylactic and therapeutic uses of the present complexes in birds for the prevention and treatment of coccidial infection.

In preparing the present complexes, bacitracin and a polyether antibiotic are combined with a non-toxic complex-forming metal ion under complex-forming conditions. Such conditions generally include a solvent in which bacitracin and the polyether antibiotic are soluble. Suitable solvents include lower primary alcohols containing up to about 4 carbon atoms, and methanol is a preferred solvent. Although the exact proportions of the starting materials may vary, it is advantageous to employ about equimolar proportions of bacitracin, metal ion, and polyether antibiotic, since bacitracin is believed to form metal complexes with polyether antibiotics at about a 1:1 ratio. The complex may be recovered from the solution in solid form by allowing the solution mixture to stand or by adding water to the solution to effect precipitation.

The bacitracin employed as a starting material is a well-known polypeptide antibiotic compound and is commercially available. Regular bacitracin is a mixture of bioactive polypeptide antibiotics which includes bacitracin A (the most active form), bacitracin B, and the bacitracin F (the inactive form).

Non-toxic complex-forming metal ions which form the present complexes include monovalent and divalent ions of Na, Co, Ni, Cu, Mn, and Zn. Preferred metal ions are $Zn^{++}$, $Mn^{++}$, $Co^{++}$ and $Ni^{++}$. The metal ions may be provided as soluble salts or, preferably, as a metal complex of the polyether antibiotic employed in the complex.

The polyether antibiotics employed as starting materials include well-known polyether antibiotic ionophores, such as lysocellin, lasolocid, naracin, monensin, carriomycin and salinomycin. Preferred polyether ionophores are lasolocid and lysocellin. Polyether ionophores are described in detail in U.S. Pat. Nos. 4,302,450; 3,839,447; 3,719,753; 3,577,531; and 3,873,715, all of which are incorporated herein by reference. Furthermore, the biology and chemistry of the polyether antibiotics are disclosed in *Polyether Antibiotics—Naturally Occurring Acid Ionophores*, Volume 1 - Biology, edited by John W. Westley, Marcel Dekker, Inc. 1982, ISBN 0-9247-1655-8 (v.1) and *Polyether Antibiotics—Naturally Occurring Acid Ionophores*, Volume 2 - Chemistry, Edited by John W. Westley, Marcel Dekker, Inc., 1983, ISBN D-8247-1888-7 (v.2).

In a preferred method for forming the complexes of this invention, a metallic salt of a polyether antibiotic and bacitracin are dissolved in a solvent. The rate and order of addition of the starting materials may vary. The solution is advantageously agitated during complex formation. The temperature and pressure may vary, and it is preferred to employ ambient temperature and pressure conditions. Depending upon the specific starting materials and solvent employed, the complex formation is usually complete in from about 0.5 to about 48 hours. The desired complex may then be recovered as a solid by (1) allowing the solution to stand at room temperature or (2) adding water to the solution to cause precipitation of the complex. The complexes precipitate from the solution as crystals or as amorphous solids. The solid complexes can then be isolated and purified by employing conventional isolation and purification techniques.

For use in controlling swine dysentery, the present complexes are administered to swine in an amount effective to control swine dysentery. The complexes are advantageously incorporated in the swine rations generally at a level of from about 15 grams per ton to about 250 grams ton. The preferred level, however, particularly in the absence of disease in the herd, is from about 40 to about 60 grams per ton for prophylaxis. However, if there has been an outbreak of the disease, or if new animals whose history is not known have been introduced into a herd, a higher level of from about 200 to about 250 grams per ton is preferred until the health of the herd is insured. Prophylactic administration of the complex is generally continued for at least about 3 days preferably at least about 21 days, and most preferably, treatment is continued until the animals are ready for market. The present complexes can also be administered by incorporation into drinking water provided for swine.

The term "feed rations" is intended to mean food provided for the animal, and it is not intended that the invention be limited thereby. Preferably, the complex is thoroughly mixed with the feed ration so that it is uniformly dispersed throughout. However, it is also contemplated that it could be sprinkled on the daily food supplies in the form of a powder or as pellets. Thus, it is not intended that the invention be limited to any particular mode of administration.

For use as growth promoters, the present complexes are administered to birds or mammals in an amount effective to promote growth of said birds or mammals. A preferred group of birds and mammals, in which an increase in growth rate is desirable, includes meat-producing birds and animals such as, for example, turkeys, chickens, beef cattle, sheep and swine.

The present complexes can be administered to birds and mammals orally in dosage forms, such as, an admixture with feed, feed concentrates or supplements and additionally in the form of boluses, capsules, tablets, suspensions or solutions containing said complexes. The present complexes can also be administered parenterally, such as, for example, intramuscularly or intravenously, or by the way of an implant which slowly releases the compound into the tissue of bloodstream of the bird or mammal in an effective growth-promoting amount. For practical reasons, it is preferred to administer the present complexes to birds or mammals by incorporation of the complexes into the bird or mammal feed.

The effective growth promoting amount of the present complexes can vary depending on many factors, such as, the size of the animal, the species of the animal, the age of the animal, the active complex used or the route of administration of the active complex.

An effective amount of a complex of this invention can be conveniently administered substantially daily throughout the growing and finishing period of the animal. "Substantially daily" administration of the active complexes described herein is meant to encompass dosage schedules, such as, for example, every other day administration and administration five or six days in a seven day period, all of which are within the scope of the present invention.

The present complexes are conveniently incorporated in a feed composition in an appropriate amount to achieve the desired daily dosage. Generally, the complexes are administered in amounts of from about 0.001 to about 0.5 milligrams per kilogram of body weight of the animal per day (mg/kg body wt/day). This amount will vary depending on the amount of feed composition consumed daily by the animal. For example, for promoting growth of poultry, one or more of the complexes are conveniently incorporated in a chicken feed composition at a concentration generally from about 10 to about 50 (preferably from about 20 to about 30) grams per ton of feed, whereas for the treatment or prophylaxis of coccidosis in chickens, a chicken feed composition generally contains from about 50 to about 200 (preferably greater than about 100) grams per ton of feed. The complexes are generally administered to ruminants in amounts of about 1 to 200, preferably about 1 to 50 mg per head per day, or in amounts sufficient to maintain a concentration of bacitracin-metal-polyether antibiotic complex in the rumen of fluid of from about 5 to about 100 parts per million by weight. For promoting growth in swine and sheep, the complexes of this invention are generally incorporated in feed composition at a concentration of from about 10–50 (preferably from about 20 to about 40) grams per ton of feed, whereas for growth promotion of beef cattle the complexes are generally added to the feed composition to a concentration of from about 15 to about 200 (preferably from about 40 to about 125) grams per ton of feed. The optimum range of an effective amount, based on the above mentioned variables, can be found using conventionally known techniques, i.e. dose titration determinations.

The complexes may also be incorporated in a mineral, protein or energy type feed additive supplement or water supply in an appropriate amount to supply an effective growth promoting daily dosage.

For commercial use, it is convenient to provide a feed additive premix, mineral supplement or concentrate containing one or more of the complexes in a proportion such that a predetermined quantity of the premix, mineral supplement or concenterate is to be added per ton of complete feed. The feed additive premix, supplement or concentrate contains one or more of the complexes of this invention and a carrier such as soybean meal or ground corn or other edible feed grade material, mineral mixtures, or innocuous diluent, such as alcohols, glycols or molasses, suitable for the animal. A concentrate may contain from about 0.001 to about 99% by weight of one or more of the present complexes in intimate admixture with an adjuvant therefor. For example, a premix, supplement or concentrate may comprise about 10% by weight (or about 50 gm/lb) of one or more of the complexes of this invention.

In further embodiments, the method of the present invention contemplates treating or dosing birds and mammals with one of the present novel compositions containing at least one of the present complexes as the active ingredient which also can be advantageously employed in combination with one or more additional animal feed additives such as, coccidiostats, antibiotics, minerals, vitamins or other compatible growth promoters employed in animal husbandry.

Examples of physiologically acceptable carriers for premix or concentrate compositions include soybean meal, corn oil, ground corn, ground corncobs, barley, wheat, mineral mixtures containing e.g., vermiculite or diatomaceous earth, corn gluten meal, corn distiller solubles or soy flour. The active complexes will be used in amounts to satisfy the criteria set forth herein. This premix or concentrate is then in turn mixed uniformly with the normal diet for the animal as desired by the growth or feed mixer. The above mentioned grains, grain mixtures, roughage feeds, usual additives, carriers and innocuous diluents constitute physiologically acceptable adjuvants for purposes of this invention.

For use in the purification of bacitracin, regular bacitracin is preferably employed as the starting material in the preparation of complexes according to this invention. For example, bacitracin can be purified from bacitracin-zinc-lasalocid complex or bacitracin-manganese lasalocid complex as a free acid or as a metal salt of bacitracin. The complexes are isolated and the bacitracin constituent or the bacitracin-metal salt constituent of the bacitracin-metal-polyether antibiotic complex is recovered from the complex. The bacitracin recovered from the complex is of a purified nature as seen by its higher unit activity per milligram when compared to the unit activity per milligram of regular bacitracin.

High performance liquid chromatography (HPLC) analysis of bacitracin that has been purified in this manner has shown that a substantial portion or all of the bacitracin F fraction is removed.

The purified bacitracin can be recovered from the complex by mixing the complex in a two-phase extractant system under acidic conditions. Such a two-phase extractant system comprises (1) an organic phase, (2) an aqueous phase. The bacitracin is extracted into the aqueous phase and is isolated by applying standard separatory techniques, such as, by adjusting the pH to near neutral and lyophilizing the aqueous filtrate thereby recovering the bacitracin as a solid. The organic phase generally comprises a water immiscible organic solvent in which the complexes are soluble. Suitable organic solvents include butanol, amyl alcohol, and the like. The two-phase extractant system may be neutralized by the addition of an acid such as, aqueous HCl.

In a particularly preferred embodiment of the present invention, regular bacitracin is purified by forming a bacitracin-zinc-lasalocid complex and isolating the bacitracin therefrom as described above. The bacitracin recovered from the bacitrain-zinc-lasalocid complex is substantially free of bacitracin F which is microbilogically inactive.

The following examples illustrate the practice of the present invention but should not be construed as limiting its scope.

STARTING MATERIALS

The bacitracin antibiotics, the polyether antibiotics and, metallic salts are well-known, readily available compounds. Metal salts of the polyether antibiotics are advantageously employed as starting materials. Such salts of the polyether antibiotics can be prepared by reacting the sodium salt of the polyether antibiotic with a metal acetate to form the desired metal salt of the polyether antibiotic. A solvent such as acetone, methanol or ethanol can be employed as the reaction medium. After the reaction is complete, water is added to the reaction mixture to precipitate the metal polyether from solution.

The following examples illustrate the preparation of various metal salts of polyether antibiotics, that are, in turn, useful for preparing the bacitracin-metal-polyether antibiotic complexes of this invention.

EXAMPLE A

Preparation of Cobalt Lysocellin

A mixture of 13.0 g (0.02 mole) of sodium lysocellin and 2.5 g of cobalt acetate dihydrate in 150 ml of ethanól was stirred and held at ambient temperature for approximately 18 hours. Two volumes of water were added to the reaction mixture slowly. A tacky semi-solid precipitate formed. On continued stirring and trituration with fresh water, a filtrable solid was obtained. The removed cobalt salt was isolated and dried (13.1 g). The product had a melting point at 119.2° C. Analysis: Calculated % Co (4.48), Found (4.54).

EXAMPLE B

Preparation of Copper Lysocellin

A mixture of 2.6 g of sodium lysocellin and 1.0 g cupric acetate monohydrate in 50 ml of acetone was stirred at room temperature until solution of solids was essentially complete. Stirring was continued and water was added slowly to precipitate the copper salt. The precipitated copper salt was isolated and dried (2.6 g). The product was recrystallized by dissolving in approximately 50 ml of methylene chloride, diluting with an equal volume of acetone, and concentrating the resulting solution at 35°–40° C. at 200–250 mm of pressure to remove the methylene chloride and most of the acetone. The resulting solid product had a melting point of 124.0° C. Analysis: Calculated % Cu (4.81); Found (3.91).

EXAMPLE C

Preparation of Nickel Lysocellin

A mixture of 6.0 g of sodium lysocellin and 2.5 g nickelous acetate tetrahydrate in 75 ml of ethanol was stirred and held at room temperature for approximately 18 hours. The reaction mixture was stirred and water added slowly to precipitate a tacky semi-solid. The product was isolated by decantation and the residue triturated with water to obtain a filterable amorphous solid. The product was isolated and dried (6.3 g). The product had a melting point of 125.3° C. Analysis: Calculated % Ni (4.47); Found (4.02).

EXAMPLE D

Preparation of Manganese Lysocellin

A mixture of 6.5 g sodium lysocellin, 2.0 g manganese chloride and 100 ml of 90% ethanol was stirred and held at ambient temperature for 18 hours. Stirring was continued and water added slowly to precipitate a tacky semi-solid. Removal of the mother liquor by decantation and trituration of the residue with fresh water gave a filterable amorphous solid which was isolated and dried (6.4 g). The product had a melting point of 112.8° C. Analysis: Calculated % Mn (4.19); Found (3.75).

EXAMPLE E

Preparation of Zinc Lysocellin

A mixture of 13.0 g of sodium lysocellin and 5.0 g zinc acetate dihydrate in 150 ml of acetone was stirred at ambient temperature for approximately 18 hours. Stirring was continued and two volumes of water were added slowly to precipitate the zinc salt. The product was isolated and dried (14.0 g). The zinc salt was recrystallized from acetone. The resulting solid product had a melting point of 102.0° C. Analysis: % Zn calculated (4.95); Found (4.37).

EXAMPLE F

Lasalocid Metal Salts

All lasalocid metal salts were prepared by the same general procedure, which is exemplified by the preparation of copper lasalocid described below.

Preparation of Copper Lasalocid

Two grams of cupric acetate monohydrate was added to a solution of 6.0 g of sodium lasalocid in 60 ml of ethanol. The resulting solution was set aside and held at ambient temperature for 18 hours. Reaction mixture was stirred and two volumes of water was added slowly to precipitate a tacky amorphous product. On continued stirring, an amorphous filterable product was obtained. The product was isolated by filtration and dried (wt. 6.3 g). All lasalocid salts prepard in this manner were used without further purification. The lasalocid salts prepared are listed in Table 1 below.

TABLE 1

| Lasalocid Salts | | |
|---|---|---|
| | | Analysis |
| Compound | % Metal | Calcd[1] | Found |
| Cobat Lasalocid | Co | 4.76 | 3.30 |
| Copper Lasalocid | Cu | 5.11 | 4.50 |
| Manganese Lasalocid | Mn | 4.45 | 3.40 |
| Nickel Lasalocid | Ni | 4.74 | 4.52 |
| Zinc Lasalocid | Zn | 5.29 | 3.95 |

[1] % Metal calculated for the di-salt

Similarly, various metal salts of the polyether antibiotics disclosed herein can be prepared employing the above described procedures.

Preparation of Complexes of the Present Invention

EXAMPLE 1

Preparation of Bacitracin-Cobalt-Lysocellin Complex

A solution of 1.3 grams (g) of cobalt lysocellin prepared as described in Example A, in 25 ml of methanol was stirred while 1.5 g of regular (reg) bacitracin (reg) was added thereto. Stirring was continued until solution of the bacitracin was complete. The reaction mixture was agitated at room temperature until precipitation of the complex occurred. The complex was isolated and recrystallized from methanol (10 ml/g) to obtain rod-like crystals.

Analysis: Calculated: C, 56.95; H, 7.74; N, 11.29; O, 19.72; S, 1.52; Co, 2.79. Found: C, 55.05; H, 8.01; N, 11.04; O, 22.52; S, 1.18; Co, 2.11.

EXAMPLE 2

Preparation of Bacitracin-Copper-Lysocellin Complex

A solution of 3.0 g of copper lysocellin, prepared as described in Example B above, in 25 ml of methanol was stirred while 2.8 g of bacitracin (reg) was added thereto. The mixture was stirred at room temperature for 1 hour. Water was added slowly to precipitate the complex. The crude complex precipitated as a tacky semi-solid which on continued stirring was recovered as a filterable amorphous solid. The crude product was slurried with ethyl acetate, isolated and dried at 40° C. under 5 millimeters (mm) Hg pressure.

Analysis: Calculated: N, 11.26; Cu, 3.00. Found: N, 11.25; Cu, 3.17.

EXAMPLE 3

Preparation of Bacitracin-Manganese-Lysocellin Complex

A solution of 6.5 g of manganese lysocellin, prepared as described in Example D above, in 60 ml of methanol was stirred while 7.0 g bacitracin (reg) was added. The solution was stirred at room temperature for four hours. Stirring was continued and water was added slowly to precipitate a tacky semi-solid. The solids were isolated by decantation and washed with fresh water to obtain a filtrable amorphous solid. The solids were isolated, washed with water and dried. The crude product was slurried with toluene (10 ml/g) to obtain an amorphous product.

Analysis: Calculated: N, 11.32; Mn, 2.61. Found: N, 10.38; Mn, 2.37.

EXAMPLE 4

Preparation of Bacitracin-Nickel-Lysocellin Complex

A solution of 2.6 g of nickel lysocellin, prepared as described in Example C above, in 25 ml of methanol was stirred while 3.0 g of bacitracin (reg) was added. Dissolution of the bacitracin was followed by precipitation of the complex. The complex was isolated and dried (2 g). A sample was recrystallized from methanol using 15 ml/g to give rod-like crystals.

Analysis: Calculated: C, 56.92; H, 7.79; N, 11.29; O, 19.72; S, 1.52; Ni, 2.78. Found: C, 55.22; H, 7.94; N, 10.94; O, 21.44; S, 1.19; Ni, 2.25.

EXAMPLE 5

Preparation of Bacitracin-Sodium-Lysocellin Complex

A solution of 13.0 g sodium lysocellin in 300 ml of methanol was stirred while 28.0 g bacitracin (reg) was added. Stirring was continued until solution of solids was complete. The resulting solution was held at room temperature for 18 hours. A precipitate formed and was collected on a filter, rinsed with methanol and dried to give 36.5 g of an amorphous product.

Analysis: Calculated: C, 57.89; H, 7.92; N, 11.48; O, 20.05; Na, 1.11. Found: C, 53.34; H, 7.87; N, 11.08; O, 22.16; Na, 0.71.

EXAMPLE 6

Preparation of Bacitracin-Zinc-Lysocellin Complex

A solution of 6.6 g of zinc lysocellin, prepared as described in Example E above, in 100 ml of methanol was stirred while 7.1 g of bacitracin (reg) was added. Stirring was continued until solution of the bacitracin was complete. The solution was held at room temperature for 72 hours. The reaction mixture was filtered to remove traces of insolubles and two volumes of water were added to the filtrate to precipitate the complex. The crude complex precipitated as a tacky semi-solid which on continued stirring was recovered as filtrable amorphous solid. The solids were isolated by filtration and dried (12.5 g). The crude product was extracted with ethylacetate, isolated and dried at 40° C. under reduced pressure.

Analysis: Calculated: N, 11.26; Zn, 3.09. Found: N, 10.63; Zn, 3.02.

EXAMPLE 7

Preparation of Bacitracin-Metal-Lasalocid Complexes

In this example, crystalline bacitracin-metal-lasalocid complexes were obtained with cobalt, copper, nickel, manganese and zinc lasalocid. Sodium lasalocid gave an amorphous product. All complexes were prepared by the same general procedure. The procedure is exemplified by the preparation of bacitracin-zinc-lasalocid.

Bacitracin-Zn-Lasalocid Complex

A solution of 2.5 g of zinc lasalocid in 50 ml of methanol was stirred and 3.0 g of regular bacitracin was added. The mixture was stirred to dissolve all solids. The resulting solution was set aside and held at ambient temperature for 24 hours. The precipitated complex was isolated, rinsed with methanol, and dried; wt. 2.3 g. Analytical sample was recrystallized from methylene chloride and methanol. The crude complex was dissolved at room temperature in a mixture of 90% methylene chloride and 10% methanol. Solution was filtered to remove traces of insoluble and the complex recovered from the filtrate by the slow addition of additional methanol. The complex was also recovered from the filtrate by the slow removal of the methylene chloride under reduced pressure at 30°–35° C.

Analytical data on the prepared bacitracin-metal-lasalocid complexes are tabulated in Table 1 below:

TABLE 1

Physical Data on the Bacitracin-Metal Lasalocid Complexes

| Metal | State | Analyses | |
|---|---|---|---|
| Co | Cryst. | Calc'd: | C, 57.98; H, 7.59; N, 11.50; O, 18.54; S, 1.55; Co, 2.84 |
| | | Found: | C, 54.20; H, 7.68; N, 10.76; O, 23.07; S, 1.39; Co, 2.61 |
| Cu | Cryst. | Calc'd: | C, 57.85; H, 7.57; N, 11.47; O, 18.50; S, 1.54; Cu, 3.06 |
| | | Found: | N/A |
| Mn | Cryst. | Calc'd: | C, 58.06; H, 7.65; N, 11.51; O, 18.57; S, 1.55; Mn, 2.66 |
| | | Found: | C, 54.24; H, 7.80; N, 10.75; O, 24.89; S, 1.13; Mn, 2.50 |
| Na | Amorph. | Calc'd: | C, 59.01; H, 7.73; N, 11.70; O, 18.87; S, 1.58; Na, 1.13 |
| | | Found: | C, 57.14; H, 7.46; N, 11.01; O, 20.17; S, 1.79; Na, 0.95 |
| Ni | Cryst. | Calc'd: | C, 57.96; H, 7.64; N, 11.49; O, 18.53; S, 1.55; Ni, 2.83 |
| | | Found: | C, 53.47; H, 7.69; N, 10.27; O, 22.51; S, 1.31; Ni, 2.40 |
| Zn | Cryst. | Calc'd: | C, 57.78; H, 7.52; N, 11.45; O, 18.47; S, 1.54; Zn, 3.14 |
| | | Found: | C, 54.36; H, 7.72; N, 10.94; O, 22.31; S, 1.57; Zn, 2.54 |

EXAMPLE 8

Purification of Bacitracin

A mixture of bacitracin-zinc-lasalocid complex (5.0 g), butanol (100 ml) and water (100 ml), adjusted to a pH of 2.0 with 10% HCl, was stirred for one hour. The layers were separated. The water layer was slurried with Amberlite ® MB-3 to adjust the pH to 6.8. The resin was removed by filtration and the aqueous filtrate was lyophilized to recover the bacitracin. High pressure liquid chromatography (HPLC) analysis of both the complex and the bacitracin recovered therefrom indicated that little or no bacitracin F was present in either sample. Regular bacitracin was also analyzed by HPLC. A comparison of HPLC data is sumarized below:

| Compound | Ratio of Peak Areas Bacitracin A/Bacitracin F to Sample Weight |
|---|---|
| Regular Bacitracin | A, 5970.4/F, 580.2 |
| Bacitracin-zinc-lasalocid complex | A, 5282.8/F,* |
| Bacitracin from Complex | A, 8228.6/F,* |

*Below detection limit

The activity of the bacitracin recovered from the bacitracin-zinc-lasalocid complex was about 85 units/mg.

EXAMPLE 9

Purification of Bacitracin

The procedures of Example 8 were repeated in all essential details, but using bacitracin-manganese lasalocid instead of bacitracin-zinc lasalocid. HPLC analysis of the bacitracin recovered indicated that very little bacitracin F was present in the purified bacitracin.

EXAMPLE 10

Purification of Zinc Bacitracin

A suspension of 5.0 g of bacitracin-zinc lasalocid complex in 50 ml of water was stirred and pH adjusted to 2.0 with 5% hydrochloric acid. Stirring continued for approximately 15 minutes and the released lasalocid acid removed by filtration, wt. 1.45 g. Filtrate was stirred and pH adjusted to 6.5 with a 10% sodium hydroxide solution. The precipitated zinc bacitracin was isolated and dried, wt. 3.3 g; % N, 12.97; % Zn, 6.35; activity, 78.0$\mu$/mg. HPLC analyses of the recovered zinc bacitracin indicated that little or no bacitracin-F was present in the purified example.

EXAMPLE 11

This example describes experimental testing of complexes of this invention for anticoccidial activity. Anticoccidial activities of test compounds were determined by administering the compounds (in feed) to chickens inoculated with active oocysts of *Eimeria tenella*. The test compounds, which are listed in Table 1 below, included four bacitracin-metal-polyether antibiotic complexes prepared according to the procedures described above. In addition, sodium lysocellin, regular bacitracin, sodium monensin, sodium lasolocid, and unmedicated inoculated and noninoculated controls were included for comparative purposes.

The test animals were Hubbard White Mountain male chicken (broiler strain) that were 5 days old at the beginning of the test. Each experimental compound was administered in a chick starter diet (Table 2) at a level of 80 g/ton and 120 g/ton. At 7 days of age, chicks were individually weighed, banded, and started on their respective treatments. Each treatment was replicated three times with five birds per replicate for a total of 15 birds per group. The test period was 10 days.

Seventy-two hours after the initiation of medication, birds were reweighed and orally inoculated with approximately 100,000 *Eimeria tenella* oocysts suspended in a 1 cc dose of saline. The following criteria were then evaluated over the next seven days:

a. morbidity (4th–6th day)
 b. mortality (4th–7th day)
 c. incidence of bloody droppings (4th–6th day)

d. body weight gain
e. feed per gain (F/G)

Results are shown in Table 3. A mild challenge was obtained with *Eimeria tenella*. At 80 and 120 g/ton, lasalocid and test compound 3 demonstrated excellent anticoccidial activity with performance near that of noninoculated controls. Birds treated with test compound 4 at 80 and 120 g/ton performed well also, however, protection against cecal bleeding normally associated with *E. tenella* infection was only fair. (There was slight bleeding in this test at 80 and 120 g/ton, and no bleeding at 200 g/ton in C-760). Monensin also demonstrated fair protection against cecal bleeding but was not tolerated well by the birds. Test compounds showed no significant anticoccidial activity at 80 or 120 g/ton, but in another test (not shown) demonstrated fair activity at 200 g/ton. The remaining compounds showed no significant amount of anticoccidial activity.

TABLE 1

Test Materials

| Identification No. | Compound |
|---|---|
| 1 | sodium lysocellin |
| 2 | bacitracin-sodium-lysocellin |
| 3 | bacitracin-zinc-lasalocid |
| 4 | bacitracin-zinc-lasalocid |
| 5 | bacitracin-zinc-lasalocid (crystalline) |
| bacitracin | regular bacitracin |
| lacalocid | sodium lasalocid |
| monensin | sodium monensin |

TABLE 2

Chick Starter Ration (23% Protein)

| | % |
|---|---|
| Ground yellow corn | 55.0 |
| Soybean meal 44% | 29.0 |
| Meat and bonemeal 50% | 5.0 |
| Fish soluble | 2.0 |
| Dehydrated alfalfa meal | 1.2 |
| Whey | 1.0 |
| Dicalcium phosphate | 1.0 |
| Super-13 mineral supplement | .8 |
| DF-broiler vitamin premix | .5 |
| Salt | .5 |
| Animal fat | 4.0 |

TABLE 3

| Test Compound | Morbidity | Mortality | Incidence of Bloody Droppings | Gain, Grams Day 0–3 | Gain, Grams Day 4–10 | F/G Day 0–3 | F/G Day 4–10 |
|---|---|---|---|---|---|---|---|
| Noninoculated Control | 0/15 | 0/15 | None | 61.3 | 242.0 | 1.77 | 1.57 |
| Lasalocid (80 g/ton) | 0/15 | 0/15 | None | 59.7 | 232.4 | 1.68 | 1.58 |
| 4 (80 g/ton) | 2/15 | 0/15 | Slight | 60.8 | 229.1 | 1.70 | 1.59 |
| 3 (120 g/ton) | 1/15 | 0/15 | None | 57.7 | 231.8 | 1.68 | 1.61 |
| 3 (80 g/ton) | 1/15 | 0/15 | None | 61.7 | 226.6 | 1.62 | 1.59 |
| 5 (120 g/ton) | 1/15 | 1/15 | Moderate | 58.8 | 228.3 | 1.72 | 1.62 |
| 4 (120 g/ton) | 1/15 | 1/15 | Slight | 58.6 | 227.7 | 1.70 | 1.59 |
| Lasalocid (120 g/ton) | 1/15 | 0/15 | None | 55.7 | 230.1 | 1.75 | 1.56 |
| Regular bacitracin | 5/15 | 0/15 | Severe | 63.7 | 212.6 | 1.62 | 1.67 |
| 5 (80 g/ton) | 4/15 | 0/15 | Moderate to Severe | 56.1 | 219.9 | 1.70 | 1.62 |
| 2 (120 g/ton) | 6/15 | 0/15 | Very Severe | 64.3 | 203.5 | 1.69 | 1.74 |
| Inoculated Control | 5/14 | 0/14 | Severe | 60.1 | 203.9 | 1.71 | 1.69 |
| 1 (120 g/ton) | 4/15 | 0/15 | Moderate | 54.1 | 209.1 | 1.81 | 1.66 |

TABLE 3-continued

| Test Compound | Morbidity | Mortality | Incidence of Bloody Droppings | Gain, Grams Day 0–3 | Gain, Grams Day 4–10 | F/G Day 0–3 | F/G Day 4–10 |
|---|---|---|---|---|---|---|---|
| 2 (80 g/ton) | 6/15 | 1/15 | Severe | 59.0 | 200.2 | 1.67 | 1.74 |
| 1 (80 g/ton) | 10/15 | 0/15 | Severe | 58.4 | 196.5 | 1.75 | 1.71 |
| Monensin | 5/15 | 0/15 | Slight | 53.2 | 202.5 | 1.81 | 1.64 |

EXAMPLE 12

The procedures of Example 11 were repeated in all essential details with the test compounds listed in Table 1 below. The results are shown in Tables 2 and 3. A satisfactory challenge was obtained with *Eimeria tenella*.

At 120 grams per ton, the bacitracin-metal-lasalocid complexes: test compounds 1, 2, 3, and 5 demonstrated good anticoccidial activity. Test compound 5 at 36 (0.30 of 120) grams per ton demonstrated fair anticoccidial activity.

Cecal bleeding associated with *E. tenella* infections was severe for 80 gram per ton treatments of test compounds 1, 2, 4, 5 and lasalocid 24 (.30 of 80) gram per ton. Despite equally severe bleeding under each of the above treatments; test compounds 1, 2, and 4, and showed weight gains appreciably higher than those of test compound 5 and lasalocid.

TABLE 1

Test Materials

| Identification No. | Complex |
|---|---|
| 1 | Bacitracin-zinc-lasalocid complex |
| 2 | Bacitracin-manganese-lasalocid complex |
| 3 | Bacitracin-nickel-lasalocid complex |
| 4 | Bacitracin-cobalt-lasalocid complex |
| 5 | Bacitracin-sodium-lasalocid complex |
| lasalocid | Sodium lasalocid |

TABLE 2

| Test Compound | Morbidity | Mortality | Incidence of Bloody Droppings | Gain/Bird Grams Day 0–3 | Gain/Bird Grams Day 4–10 | F/G Day 0–3 | F/G Day 4–10 |
|---|---|---|---|---|---|---|---|
| Noninoculated Control | 0/14 | 0/14 | None | 56.6 | 229.6 | 1.78 | 1.61 |
| Lasalocid (120 g/ton) | 0/15 | 0/15 | None | 52.1 | 225.2 | 1.76 | 1.52 |
| Lasalocid (80 g/ton) | 1/15 | 0/15 | None | 58.0 | 219.4 | 1.71 | 1.60 |
| 3 (120 g/ton) | 2/15 | 0/15 | Slight-Moderate | 61.3 | 202.4 | 1.58 | 1.74 |
| 2 (120 g/ton) | 4/15 | 0/15 | Slight-Moderate | 57.0 | 198.7 | 1.75 | 1.74 |
| 1 (120 g/ton) | 4/15 | 0/15 | Slight- | 59.0 | 188.4 | 1.64 | 1.78 |
| 4 (120 g/ton) | 5/15 | 0/15 | Slight-Moderate | 59.5 | 187.4 | 1.69 | 1.72 |
| 1 (80 g/ton) | 6/15 | 0/15 | Severe | 61.6 | 180.1 | 1.62 | 1.86 |
| Lasalocid (36 g/ton) | 5/14 | 1/14 | Moderate | 61.5 | 176.5 | 1.74 | 1.86 |
| 2 (80 g/ton) | 5/15 | 0/15 | Severe | 60.5 | 171.5 | 1.68 | 1.92 |
| 5 (120 g/ton) | 8/15 | 0/15 | Moderate | 58.6 | 169.7 | 1.65 | 1.83 |
| 4 (80 g/ton) | 9/15 | 0/15 | Severe | 63.3 | 164.1 | 1.61 | 1.91 |

TABLE 2-continued

| | | | | | | | |
|---|---|---|---|---|---|---|---|
| 3 (80 g/ton) | 10/15 | 0/15 | Moderate | 61.3 | 154.0 | 1.81 | 2.01 |
| 5 (80 g/ton) | 11/15 | 0/15 | Severe | 59.9 | 147.7 | 1.68 | 2.12 |
| Lasalocid, (24 g/ton) | 9/15 | 0/15 | Severe | 58.7 | 148.5 | 1.78 | 2.09 |
| Inoculated Control | 12/15 | 0/15 | Very Severe | 56.9 | 132.4 | 1.83 | 2.41 |

| Test Compound | Cecal Bleeding | Gain/Bird Days 0–3 | Feed/Gain Days 0–3 | Gain/Bird Days 4–10 | Feed/Gain Days 4–10 |
|---|---|---|---|---|---|
| *36 g/ton Lasalocid (Approx.)* | | | | | |
| Lasalocid | Moderate | 61.5 | 1.74 | 176.5 | 1.86 |
| 3 | Slight-Moderate | 61.3 | 1.58 | 202.4 | 1.74 |
| 2 | Slight-Moderate | 57.0 | 1.75 | 198.7 | 1.74 |
| 1 | Slight | 59.0 | 1.65 | 188.4 | 1.78 |
| 4 | Slight-Moderate | 59.5 | 1.69 | 187.4 | 1.72 |
| 5 | Moderate | 58.6 | 1.65 | 169.4 | 1.83 |
| *14 g/ton Lasalocid (Approx.)* | | | | | |
| Lasalocid | Severe | 58.7 | 1.78 | 148.5 | 2.09 |
| 1 | Severe | 61.6 | 1.62 | 180.1 | 1.86 |
| 2 | Severe | 60.5 | 1.68 | 171.5 | 1.92 |
| 4 | Severe | 63.3 | 1.61 | 164.1 | 1.91 |
| 3 | Moderate | 61.3 | 1.81 | 154.0* | 2.01* |
| 5 | Severe | 59.9 | 1.68 | 147.7 | 2.12 |

*Birds were without water for several hours which may have adversely influenced these figures.

EXAMPLE 13

This example describes experimetnal testing of complexes of the present invention as feed additives for improving weight gain or feed utilization efficiency in birds. Test animals were male meat-type chickens (Hubbard strain). Fluorescent room lights were on a 16 hours light/8 hours dark schedule. The chicks were allotted to the pens on the basis of weight classes, and chicks in the even numbered pens were wing banded. Group weights were obtained at the start and individual weights at the termination of the experiment. Chicks weighing between 55 and 65 grams were selected for the test. The test compounds are shown in Table 1 below. The test compounds were blended with a basal feed ration (shown in Table 2) at the indicated concentration. Birds fed medicated feed and feed supplemented with zinc bacitracin (Baciferm ® 50, International Minerals and Chemical Corp.) were used as controls. The test was continued for 11 days, after which individual weights, pen weight and feed consumption were recorded and analyzed.

The results of the test are shown in Tables 3 and 4 below. Each of the bacitracin-metal-polyether antibiotic complexes produced improved weight gains compared to unmedicated controls. Some of the complexes also seemed to improve feed utilization efficiencies; however, statistical comparison of each test group to unmedicated controls (Table 4) shows only test compound 6 to produce a significant imporvement in feed utilization efficiency.

TABLE 1

Treatment Numbers and Supplement Identification

| Test Compound No. | Rye Basal Diet[a] |
|---|---|
| 1 | Unmedicated |
| 2 | .00275% Bacitracin (zinc)[b] |
| 3 | .00275% Bacitracin-Zn-Lasalocid |
| 4 | .00275% Bacitracin-Zn-Lasalocid |
| 5 | .00275% Bacitracin-Zn-Lasalocid |
| 6 | .00275% Bacitracin-Na-Lasalocid |
| 7 | .00275% Bacitracin-Na-Lasalocid |
| 8 | .0055% Bacitracin-Zn-Lasalocid |
| 9 | .0055% Bacitracin-Zn-Lasalocid |
| 10 | .0055% Bacitracin-Na-Lasalocid |
| 11 | .0055% Bacitracin-Na-Lasalocid |

[a]See Table 2
[b]BACIFERM 50 = 11.01% active ingredient

TABLE 2

Basal Ration Composition

| Ingredient | % |
|---|---|
| Ground Rye (var. Gazelle) | 57.04974 |
| Soybean meal - 49% | 27.25 |
| Fish meal - 60% | 4.00 |
| Meat and bone - 50% | 4.00 |
| Alfalfa meal - 17% | 1.25 |
| Dried whey | 1.00 |
| Practical diet vit/Tm | .56026 |
| Iodized salt | .22 |
| $CaCo_3$, Miss #6 | .3572 |
| Dyanfos, 2262 Phosphate Supplement | .2728 |
| DL-Methionine | .05 |
| Animal fat | 4.00 |

TABLE 3

Average Gain and Feed Utilization Data and Indexes

| Test Compound | Average Gain, g | Index | Gain/Feed Ratio | Index |
|---|---|---|---|---|
| 1 | 206 | 100 | 63.7 | 100 |
| 2 | 220 | 107 | 65.5 | 102.8 |
| 3 | 215 | 104.5 | 64.6 | 101.3 |
| 4 | 217 | 105.4 | 62.8 | 98.5 |
| 8 | 213 | 103.2 | 63.0 | 98.8 |
| 5 | 214 | 104.2 | 63.1 | 99.0 |
| 9 | 216 | 104.7 | 64.0 | 100.4 |
| 6 | 219 | 106.6 | 66.7 | 104.7 |
| 10 | 219 | 106.3 | 63.7 | 99.9 |
| 7 | 225 | 109.4 | 65.6 | 103.0 |
| 11 | 217 | 105.5 | 62.9 | 98.8 |

TABLE 4

Statistical Comparison of Treatment Totals

| Treatment | Average Weight | F | Probability | Gain/Feed | F | Probability |
|---|---|---|---|---|---|---|
| 1 vs | 266.3 | | | 63.7 | | |
| 2 | 280.2 | 4.799 | <.05(.029) | 65.5 | 1.410 | NS(.243) |
| 3 | 274.8 | 1.856 | NS(.174) | 64.6 | .310 | NS(.581) |
| 4 | 277.0 | 2.818 | <.10(.094) | 62.8 | .410 | NS(.526) |
| 8 | 272.4 | .931 | NS(.335) | 63.0 | .231 | NS(.634) |
| 5 | 274.8 | 1.806 | NS(.18) | 63.1 | .178 | NS(.685) |
| 9 | 275.3 | 2.024 | NS(.16) | 64.0 | .025 | NS(.874) |
| 6 | 279.4 | 4.255 | <.05(.0399) | 66.7 | 3.945 | .055 |
| 10 | 279.1 | 4.094 | <.05(.044) | 63.7 | .0005 | NS(.982) |
| 7 | 285.6 | 9.286 | <.01(.0025) | 65.6 | 1.615 | NS(.212) |
| 11 | 277.2 | 2.935 | <.10(.088) | 62.9 | .266 | NS(.609) |

NS - not significantly different.

EXAMPLE 14

The procedures of Example 13 were repeated in all essential details with the test compounds listed in Table 1 below. All of the bacitracin-metal-polyether antibiotic complexes tested produced statistically significant increases in gains compared to the unmedicated basal ration.

The test involving test compounds 1 and 3-14 consisted of 5 replicates of 7 chicks and those involving test compound 2 consisted of 6 replicates of 7 chicks. The tests were continued for 12 days, after which individual weight gains and feed conusumption were recorded and analyzed.

The test results are shown in Table 2 below, which also show comparisons of the data to unmedicated feed and to feed supplements with zinc bacitracin.

TABLE 1

| Test Compound | Sample Identification |
|---|---|
| 1 | Unmedicated |
| 2 | Bacitracin as zinc bacitracin supplied by BACIFERM ® -50, 52.1 g/lb = 11.457% active ingredient (Concentration of active ingredient in feed = .0033%) |
| 3 | Lysocellin acid, .0066% |
| 4 | Sodium-zinc-lysocellin, .0066% |
| 5 | Bacitracin-sodium-lasalocid, .0066% |
| 6 | Bacitracin-sodium-lysocellin, .0066% |
| 7 | Bacitracin-zinc-lysocellin, .0066% |
| 8 | Bacitracin-zinc-lasalocid, .0066% |
| 9 | Bacitracin-manganese-lasalocid, .0066% |
| 10 | Bacitracin-nickel-lasalocid, .0066% |
| 11 | Bacitracin-cobalt-lasalocid, .0066% |
| 12 | Bacitracin-cobalt-lysocellin, .0066% |
| 13 | Bacitracin-nickel-lysocellin, .0066% |
| 14 | Bacitracin-copper-lysocellin, .0066% |
| 15 | Bacitracin-manganese-lysocellin, .0066% |

TABLE 2

Experimental Data - Averages of 5 or 6 Replicates

| Treatment | Data | Relative to #1 Index | P = | Relative to #2 Index | P = |
|---|---|---|---|---|---|
| Gains/gram | | | | | |
| 1 | 185.1 | 100 | — | 88.3 | <.001 |
| 2 | 209.6 | 113.2 | <.001 | 100 | — |
| 3 | 202.0 | 109.1 | .009 | 96.4 | .188 |
| 4 | 197.2 | 106.5 | .051 | 94.1 | .038 |
| 5 | 212.4 | 114.8 | <.001 | 101.3 | .620 |
| 6 | 213.8 | 115.5 | <.001 | 102.0 | .452 |
| 7 | 213.5 | 115.3 | <.001 | 101.9 | .491 |
| 8 | 212.4 | 114.8 | <.001 | 101.3 | .610 |
| 9 | 218.2 | 117.9 | <.001 | 104.1 | .136 |
| 10 | 211.6 | 114.3 | <.001 | 100.9 | .712 |
| 11 | 213.5 | 115.3 | <.001 | 101.9 | .489 |
| 12 | 213.4 | 115.3 | <.001 | 101.8 | .493 |
| 13 | 220.4 | 119.1 | <.001 | 105.2 | .067 |
| 14 | 211.0 | 114.0 | <.001 | 100.7 | .804 |
| 15 | 207.4 | 112.0 | .001 | 98.9 | .695 |
| Gain/Feed | | | | | |
| 1 | .563 | 100 | — | 94.5 | .008 |
| 2 | .596 | 105.9 | .008 | 100.0 | — |
| 3 | .588 | 104.4 | .041 | 98.6 | .520 |
| 4 | .585 | 103.9 | .076 | 98.2 | .340 |
| 5 | .595 | 105.7 | .013 | 99.8 | .950 |
| 6 | .609 | 108.2 | .001 | 102.2 | .22 |
| 7 | .609 | 108.2 | .001 | 102.2 | .22 |
| 8 | .599 | 106.4 | .006 | 100.5 | .78 |
| 9 | .607 | 107.8 | .001 | 101.8 | .29 |
| 10 | .606 | 107.6 | .002 | 101.7 | .35 |
| 11 | .597 | 106.0 | .008 | 100.2 | .88 |
| 12 | .605 | 107.5 | .002 | 101.5 | .37 |
| 13 | .593 | 105.3 | .019 | 99.5 | .81 |
| 14 | .594 | 105.5 | .014 | 99.7 | .92 |
| 15 | .600 | 106.6 | .005 | 100.7 | .68 |

EXAMPLE 15

Ruminal Activity

A low acetate/propionate ratio in an incubated mixture of bacitracin-metal polyether antibiotic complexes and digestive fluids from a fistulated steer indicates that the complexes may enhance growth and improve feed utilization in rumanants. Rumen fluid was removed from a fistulated steer and strained through a cheesecloth. An equal amount of pH 7 buffer was added to strained rumen fluid. After layering occurred, the lower layer was saved and again diluted with equal amount of buffer. Ten ml. portions of buffered rumen fluid were added to fermentation vessels containing 500 mg. fresh finely ground cattle ration, 1 mg cellubiose and a test compound listed in Table 1 below at the indicated concentration. The fermentation vesels were outfitted with one-way gas valves, placed in an incubator and shaken for 24 hours at 38° C. Fermentation was stopped by addition of 1 ml mercuric chloride. The liquid was decanted and analyzed for volatile fatty acids by gas chromatography. Test results are summarized in Table 1, wherein Bac=bacitracin.

TABLE 1

Rumen Screen - In Vitro Studies on the Effect of Bacitracin Lysocellin Complexes on Ruminal Volatile Fatty Acid Ratio

| Compound Description | A/P Ratio |
|---|---|
| Neg. Control | 1.39 |
| Zinc Bacitracin (5 ppm) | 1.15 |
| Sodium Lysocellin (5 ppm) | 1.07 |
| Bac-Co Lysocellin (10 ppm) | 1.10 |
| Bac-Ni Lysocellin (10 ppm) | 1.10 |

EXAMPLE 16

The procedures of Example 15 were repeated in all essential details with the test compounds and concentrations listed in Table 1 below, as are the results of the test.

TABLE 1

Rumen Screen - In Vitro Studies on the Effect of Bacitracin-Metal-Polyether Complexes on Ruminal Volatile Fatty Acid Ratio

| Compound Description | A/P Ratio |
|---|---|
| Neg. Control | 1.39 |
| Zinc Bacitracin (5 ppm) | 1.15 |
| Sodium Lysocellin (5 ppm) | 1.07 |
| Bac-Ni Lysocellin Complex (10 ppm) | .88 |
| Bac-Zn Lysocellin Complex (10 ppm) | 1.14 |

EXAMPLE 17

Antidysentery Activity

Bacitracin-metal-lysocellin complexes were screened in vitro against nine field strains of *Treponema hyodysenteriae*.

The complexes were incorporated at the concentrations indicated in Table 1 below in a mixture of trypticase soy agar and 5% fresh whole bovine blood. The mixtures were added to petri dishes and streaked with culture derived from field isolates of *T. hyodysenteriae*. The streaked dishes were incubated under anaerobic conditions for 40 hours and checked for growth. Lack of growth indicates the inhibitory endpoint (effective concentration of complex).

Test results are summarized in Table 1 below, and indicate the usefulness of the tested complexes in the area of animal health.

TABLE 1

Antitreponema Hyodysenteriae Activity
Bacitracin-Metal-Lysocellin Complexes
Inhibitory Endpoint, μg/ml

| Complex metal | 1 | 2 | 3 | 4 | 5 | 6 | 7 | 8 | 9 |
|---|---|---|---|---|---|---|---|---|---|
| Na | 1.0–5.0 | 1.0–5.0 | 1.0–5.0 | 1.0–5.0 | 1.0–5.0 | 1.0–5.0 | 1.0–5.0 | 1.0–5.0 | 1.0–5.0 |
| Mn | 1.0–5.0 | 1.0–5.0 | 10–50 | 10–50 | 10–50 | 10–50 | 10–50 | 10–50 | 10–50 |
| Zn | 0.1–0.5 | 1.0–5.0 | 1.0–5.0 | 0.5–1.0 | 1.0–5.0 | 1.0–5.0 | 1.0–5.0 | 1.0–5.0 | 1.0–5.0 |
| Ni | 0.1–5.0 | 1.0–5.0 | 0.1–0.5 | 0.1–0.5 | 0.1–0.5 | 0.5–1.0 | 0.5–1.0 | 0.5–1.0 | — |
| Co | 0.5–1.0 | 0.5–1.0 | 0.1–0.5 | 1.0–5.0 | 1.0–5.0 | 1.0–5.0 | 1.0–5.0 | 1.0–5.0 | 1.0–5.0 |
| Cu | 1.0–5.0 | 1.0–5.0 | 0.5–1.0 | 1.0–5.0 | 1.0–5.0 | 1.0–5.0 | 1.0–5.0 | 1.0–5.0 | 1.0–5.0 |

EXAMPLE 18

The procedures of Example 17 were repeated in all essential details with the test compounds and results shown in Table 1 below.

TABLE 1

Antitreponema Hyodysenteriae Activity
Bacitracin—Metal-Lasalocid Complexes
Inhibitory Endpoint, μg/ml

| Complex Metal | 1 | 2 | 3 | 4 | 5 | 6 | 7 | 8 | 9 |
|---|---|---|---|---|---|---|---|---|---|
| Na | 1.0–5.0 | 0.5–1.0 | 1.0–5.0 | 1.0–5.0 | 1.0–5.0 | 1.0–5.0 | 1.0–5.0 | 1.0–5.0 | 1.0–5.0 |
| Mn | 1.0–5.0 | 1.0–5.0 | 1.0–5.0 | 1.0–5.0 | 1.0–5.0 | 1.0–5.0 | 10–50 | 5.0–10.0 | 5.0–10.0 |
| Co | 5.0–10.0 | 1.0–5.0 | 0.5–1.0 | 0.5–1.0 | 1.0–5.0 | 1.0–5.0 | 1.0–5.0 | 1.0–5.0 | 1.0–5.0 |
| Na | 1.0–5.0 | 1.0–5.0 | 1.0–5.0 | 0.1–0.5 | 1.0–5.0 | 1.0–10.0 | 1.0–5.0 | 1.0–5.0 | — |
| Cu | 1.0–5.0 | 1.0–5.0 | 5.0–10.0 | 5.0–10.0 | 1.0–5.0 | 5.0–10.0 | 10–50 | 10–50 | 10–50 |
| Zn | 5.0–10.0 | 5.0–10.0 | 1.0–5.0 | 1.0–5.0 | 1.0–5.0 | 5.0–10.0 | 10–50 | 5.0–10.0 | 5.0–10.0 |
| Ni | 10–50 | 5.0–10.0 | 1.0–5.0 | 1.0–5.0 | 1.0–5.0 | 1.0–5.0 | 1.0–5.0 | 1.0–5.0 | 1.0–5.0 |

I claim:

1. A complex of bacitracin, a polyether antibiotic ionophore and a non-toxic complex-forming metal ion, said complex being crystalline.

2. The complex of claim 1, wherein the bacitracin antibiotic is bactracin A, bacitracin B, or a mixture thereof.

3. The complex of claim 1, wherein the metal is Na, Co, Cu, Mn, Ni, or Zn.

4. The complex of claim 2, wherein the metal is Mn or Zn.

5. The complex of claim 4, wherein the bacitracin antibiotic is bacitracin A and the polyether antibiotic is lasalocid.

6. The complex of claim 5, wherein the metal is Zn.

7. The complex of claim 4, wherein the metal is Zn.

8. The complex of claim 1, wherein the bacitracin antibiotic is substantially free of bacitracin F, the polypolyether antibiotic is lasalocid and the metal is Zn.

9. A complex of bacitracin, a polyether antibiotic ionophore and a non-toxic complex-forming metal ion, said complex being substantially free of bacitracin F.

10. The complex of claim 9, wherein the bacitracin antibiotic is bacitracin A, bacitracin B, or a mixture thereof.

11. The complex of claim 9, wherein the metal is Na, Co, Cu, Mn, Ni, or Zn.

12. The complex of claim 10, wherein the metal is Mn or Zn.

13. The complex of claim 12, wherein the bacitracin antibiotic is bacitracin A and the polyether antibiotic is lasalocid.

14. The complex of claim 13, wherein the metal is Zn.

15. The complex of claim 14, wherein said complex is of a crystalline nature.

16. The complex of claim 12, wherein the metal is Zn.

17. The complex of claim 9, wherein the polyether antibiotic is lasalocid and the metal is Zn.

* * * * *

UNITED STATES PATENT AND TRADEMARK OFFICE
CERTIFICATE OF CORRECTION

PATENT NO. : 4,693,992

DATED : September 15, 1987

INVENTOR(S) : Vernon V. Young

It is certified that error appears in the above-identified patent and that said Letters Patent are hereby corrected as shown below:

Column 2, line 50, delete "Westley," second occurrence

Column 3, line 48, "of" first occurrence, should read -- or --

Column 4, line 40, "concenterate" should read -- concentrate --

Column 6, line 11, "filtrable" should read -- filterable --

Column 7, Table 1, column 1, line 1, "Cobat" should read -- Cobalt --

Column 7, line 19, "prepard" should read -- prepared --

Column 8, line 13, "filtrable" should read -- filterable --

Column 12, line 27, delete "and" second occurrence

Column 13, line 19, Table 2, "14 g/ton Lasalocid (Approx.)" should read -- 24 g/ton Lasalocid (Approx.) --

Column 13, line 30, "experimetnal" should read -- experimental --

Column 13, line 57, "imporvement" should read -- improvement --

Column 15, line 5, "conusumption" should read -- consumption --

Column 16, line 2, "rumanants" should read -- ruminants --

UNITED STATES PATENT AND TRADEMARK OFFICE
CERTIFICATE OF CORRECTION

PATENT NO. : 4,693,992
DATED : September 15, 1987
INVENTOR(S) : Vernon V. Young

It is certified that error appears in the above-identified patent and that said Letters Patent is hereby corrected as shown below:

Column 16, line 12, "vesels" should read -- vessels --
Column 18, Claim 8, line 3, "polypolyether" should read -- polyether --

Signed and Sealed this

Thirty-first Day of May, 1988

Attest:

Attesting Officer

DONALD J. QUIGG

Commissioner of Patents and Trademarks